United States Patent [19]

Koch

[11] Patent Number: 5,027,830
[45] Date of Patent: Jul. 2, 1991

[54] METHOD OF PREPARING A CERVICAL CAP

[76] Inventor: James P. Koch, 211 Sargent Rd., Brookline, Mass. 02146

[21] Appl. No.: 511,101

[22] Filed: Apr. 19, 1990

Related U.S. Application Data

[63] Continuation-in-part of Ser. No. 195,497, May 18, 1988, abandoned, which is a continuation-in-part of Ser. No. 50,230, May 14, 1987, abandoned.

[51] Int. Cl.$^5$ ............................................. A61F 6/08
[52] U.S. Cl. ..................................... 128/841; 128/837
[58] Field of Search ............................... 128/834–841; 446/224

[56] References Cited

U.S. PATENT DOCUMENTS

| | | | |
|---|---|---|---|
| 1,092,417 | 7/1869 | Angell | 128/835 |
| 1,103,114 | 7/1914 | Warren | 128/834 |
| 1,169,804 | 2/1916 | Gregory | 446/224 |
| 3,952,737 | 4/1976 | Lipfert | 128/837 |
| 4,007,249 | 2/1977 | Erb | 128/837 X |
| 4,320,751 | 3/1982 | Loeb | 128/837 |
| 4,322,463 | 3/1982 | Goepp | 128/841 X |
| 4,326,510 | 4/1982 | Buckles | 128/837 X |
| 4,363,318 | 12/1982 | Goepp | 128/837 |

FOREIGN PATENT DOCUMENTS

| | | |
|---|---|---|
| 385401 | 12/1921 | Fed. Rep. of Germany . |
| 414541 | 7/1923 | Fed. Rep. of Germany . |
| 557914 | 8/1932 | Fed. Rep. of Germany . |
| 734071 | 10/1932 | France . |
| 198122 | 9/1932 | Sweden . |
| 243186 | 11/1925 | United Kingdom . |
| 680192 | 10/1952 | United Kingdom . |

Primary Examiner—Robert A. Hafer
Assistant Examiner—Kevin G. Rooney
Attorney, Agent, or Firm—Fish & Richardson

[57] ABSTRACT

A contraceptive cervical cap or form therefor, and a method for producing the same.

6 Claims, 4 Drawing Sheets

METHOD OF PREPARING A CERVICAL CAP

BACKGROUND OF THE INVENTION

This application is a continuation-in part of Koch, U.S.S.N. 195,497, now abandoned, filed May 18, 1988 entitled "Cervical Cap", which is a continuation in-part of Koch, U S.S.N. 050,230, filed May 14, 1987 entitled "Cervical Cap", now abandoned. The invention relates to contraceptive cervical caps.

Cervical caps are contraceptive devices that fit over the cervix and physically block the inflow of semen, thus preventing pregnancy.

Loeb, U.S. Pat. No. 4,320,751, describes a cervical cap in which the inner surface is covered with a foam lining to provide a better fit to the cervix. An elastomeric web at the cap's apex forms a pressure-operated valve to permit outflow of uterine discharges, e.g., menstrual flow, but not inflow of semen.

Lipfert et al., U.S. Pat. No. 3,952,737, describes a cervical cap with a pressure-operated "collapsed elastomeric tube valve" with a slit at the outer end to permit outflow but not inflow. At col. 6, lines 34–43, Lipfert states that "[f]low is permitted through [the] slit . . . but pressure from the outside of [the tube's] end . . . keeps [the] slit . . . normally closed and prevents back flow." Two "internal bead formations," one on the lip portion and one in the body of the cap, help clamp the cap to the cervix.

SUMMARY OF THE INVENTION

In general, the invention features, in one aspect, a contraceptive cervical cap that includes a rim portion for securing the cap to a woman's cervix; and a dome portion that includes a solid biocompatible material (i.e., a material that is non-toxic when placed in contact with biological tissue) adapted to contact the surface of the cervix throughout its extent when the cap is in place such that the gap between the interior surface of the dome portion and the cervix normally present when the cap is in place is completely eliminated.

In a second aspect, the invention features a method for preparing a contraceptive cervical cap or a mold therefor, involving fitting a cervical cap to the cervix of the patient, the cap including a rim portion for securing it to the cervix, a dome portion with input means for introducing a biocompatible material into the dome portion, and venting means for removing displaced air and excess biocompatible material during introduction, the dome portion being spaced from the cervix when the cap is in place to form a gap between the interior surface of the dome portion and the cervix; and filling the gap of the dome portion with the biocompatible material through the input means. In preferred embodiments, the cap further includes flow control means for permitting material to flow out of, but not into, the cervix and uterus through the cap. Preferably, the flow control means includes a collapsed elastomeric tube attached at one end to the dome portion of the cap, the tube being aligned with and in communication with the cervical canal (i.e. the passageway connecting the uterus with the vagina), the dimensions of the tube being sufficient to permit outflow of uterine and cervical material but not inflow of sperm. The tube and/or the biocompatible material may be infused with a spermicide.

The biocompatible material filling the gap between the cervix and the interior surface of the cap's dome portion preferably is a silicone elastomer and the rim portion of the cap preferably includes a plurality of ridges arranged along the interior surface of the rim portion to secure the cap to the cervix. In addition, the cap preferably further includes input means for introducing the biocompatible material into the dome portion when the cap is in place and venting means for removing displaced air and excess gap-filling material during introduction.

During preparation of the cap or a mold therefor, a marker is inserted into the cervical canal prior to the fitting step to mark the canal's location. The marker then embeds in the biocompatible material during the filling step. Next, the cap is removed from the cervix and an opening created in the dome portion at the position of the marker corresponding to the location of the cervical canal to permit material to flow out of, but not into, the cervix and uterus through the cap.

In another aspect, the invention features a method of preparing a contraceptive cervical cap or a form therefor that includes the steps of providing a cervical cap that includes a rim portion for securing the cap to the cervix and a dome portion having input means for introducing a biocompatible material into the cap, the dome portion being spaced from the cervix when the cap is in place to form a gap between the interior surface of the dome portion and the cervix;

placing the cap over the cervix loosely while leaving an amount of space between the rim portion of the cap and the cervix through which excess biocompatible material can leave the cap;

filling the cap with the biocompatible material through the input means;

sealing the rim portion of the filled cap around the cervix; and withdrawing a predetermined amount of the biocompatible material through the input means to draw the cervix out into the biocompatible material.

In preferred embodiments, the rim portion of the cap includes a plurality of ridges arranged along its interior surface to secure the cap to the cervix. The preferred biocompatible material is a silicone elastomer. The preferred input means includes a tube in communication with the dome portion of the cap and a syringe attached to the tube. The amount of biocompatible material withdrawn from the filled cap is preferably about equal to the volume of the cervix.

During the preparation of the cap or form therefor, a marker is preferably inserted into the cervical canal prior to placing the cap over the cervix to mark the canal's location. The marker is then embedded in the biocompatible material during introduction of the biocompatible material into the cap. The cap is removed from the cervix after the predetermined amount of biocompatible material has been withdrawn and an opening is created in the dome portion at the position of the marker, corresponding to the location of the cervical canal, to permit material to flow out of, but not into, the cervix and uterus through the cap.

The contraceptive cervical cap of the invention can be worn for extended periods of time. The gap filling material causes a suction cup effect between the cap and the cervix, thereby preventing the cap from dislodging; the ridges on the interior of the rim portion further secure the cap to the cervix. The gap filling material also prevents infection-causing bacteria from building up in the gap during extended wear, and also inhibits sperm that might penetrate the rim portion from entering the cervical canal. The collapsed elastomeric tube permits the outflow of uterine and cervical discharges but not the inflow of sperm, without relying on pressure operation. Furthermore, the cap can be readily customlined with the biocompatible material to accomodate each patient.

Withdrawing some of the biocompatible material from the filled cap creates a vacuum which draws the cervix out into the biocompatible material, thereby counteracting the cervix's tendency to retract into the pelvis when the biocompatible material pushes against it during introduction. Drawing the cervix into the biocompatible material creates an accurate impression of the cervix inside the cap and thus ensures accurate fit of the final filled cap.

Other features and advantages of the invention will be apparent from the following description of the preferred embodiments thereof, and from the claims.

DESCRIPTION OF THE PREFERRED EMBODIMENTS

We first briefly describe the drawings.

STRUCTURE

Figure 1:
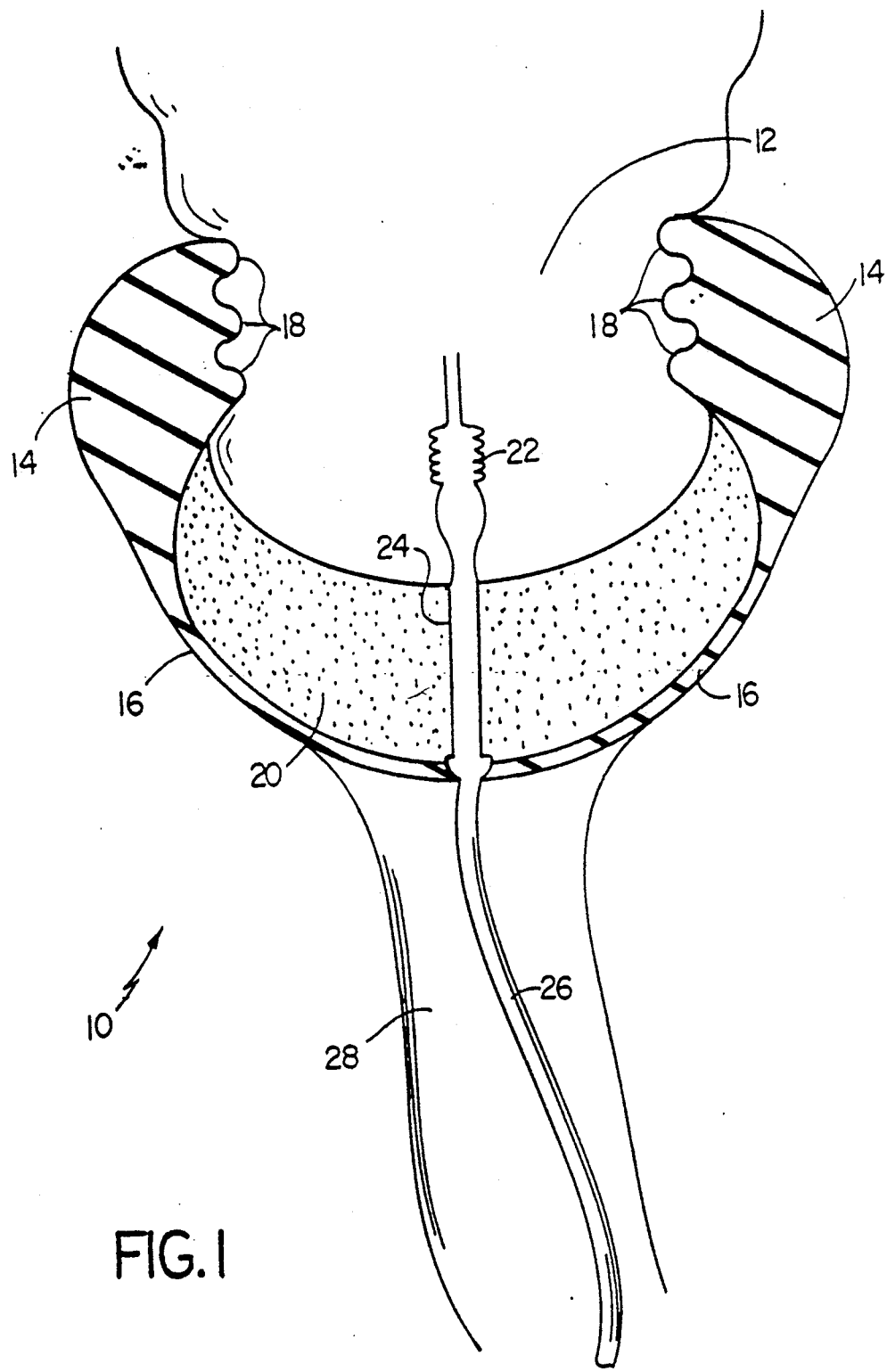
FIG. 1 is a cross-sectional view of a contraceptive cervical cap fitted over a patient's cervix.

There is shown in FIG. 1 contraceptive cervical cap 10 made of a flexible material, e.g., natural or synthetic rubber, secured to the cervix 12 of a female patient. Cap 10 includes a rim portion 14 and a dome portion 16. Rim portion 14 includes vertically spaced ridges 18 arranged along its interior surface for engaging cervix 12 at indentations that ridges 18 form in the cervical wall; preferably, ridges 18 extend around the entire circumference of rim portion 14. Ridges 18 grasp cervix 12 firmly to prevent cap 10 from dislodging once in place.

Dome portion 16 does not contact cervix 12 when cap 10 is properly fitted, so that there is a gap 20 between its interior surface and cervix 12. Gap 20 is filled with a solid, flexible, biocompatible material free from pores. Preferred materials include alginate and polymers, e.g., polysiloxanes such as silicone elastomers (e.g., A-101 medical grade elastomer available from Factor II, Lakeside, Ariz.). The polymer creates a suction cup effect between dome portion 16 and cervix 12, thereby forming a seal that further prevents cap 10 from dislodging. The polymer also prevents the build-up of potentially infection-causing bacteria that normally accumulate in the unfilled gap, and also prevents any sperm that penetrate rim portion 14 from entering cervical canal 22.

Effluent canal 24 (diameter = 1-10 mm) drilled through the solid polymer and dome portion 16, and aligned with cervical canal 22, connects canal 22 with one end of a collapsed elastomeric effluent tube 26 (diameter = approximately 4-12 mm), which is open at both ends. Tube 26 typically is fabricated from natural or synthetic rubber, and may extend the length of vagina 28. The end of tube 26 joining tube 26 with cap 10 may be flanged and wedged between the polymer and interior surface of dome portion 16 to hold tube 26 in place. Uterine and cervical discharges, e.g., menstrual flow, are permitted to flow through cervical canal 22, effluent canal 24, and tube 26, and out of the body, allowing cap 10 to be worn for extended periods of time. However, because of the small diameter, long length, collapsed condition, and electrostatic properties of tube 26, retrograde migration of sperm through tube 26 and into cervical canal 22 is prevented.

Manufacture and Use

Figure 2:
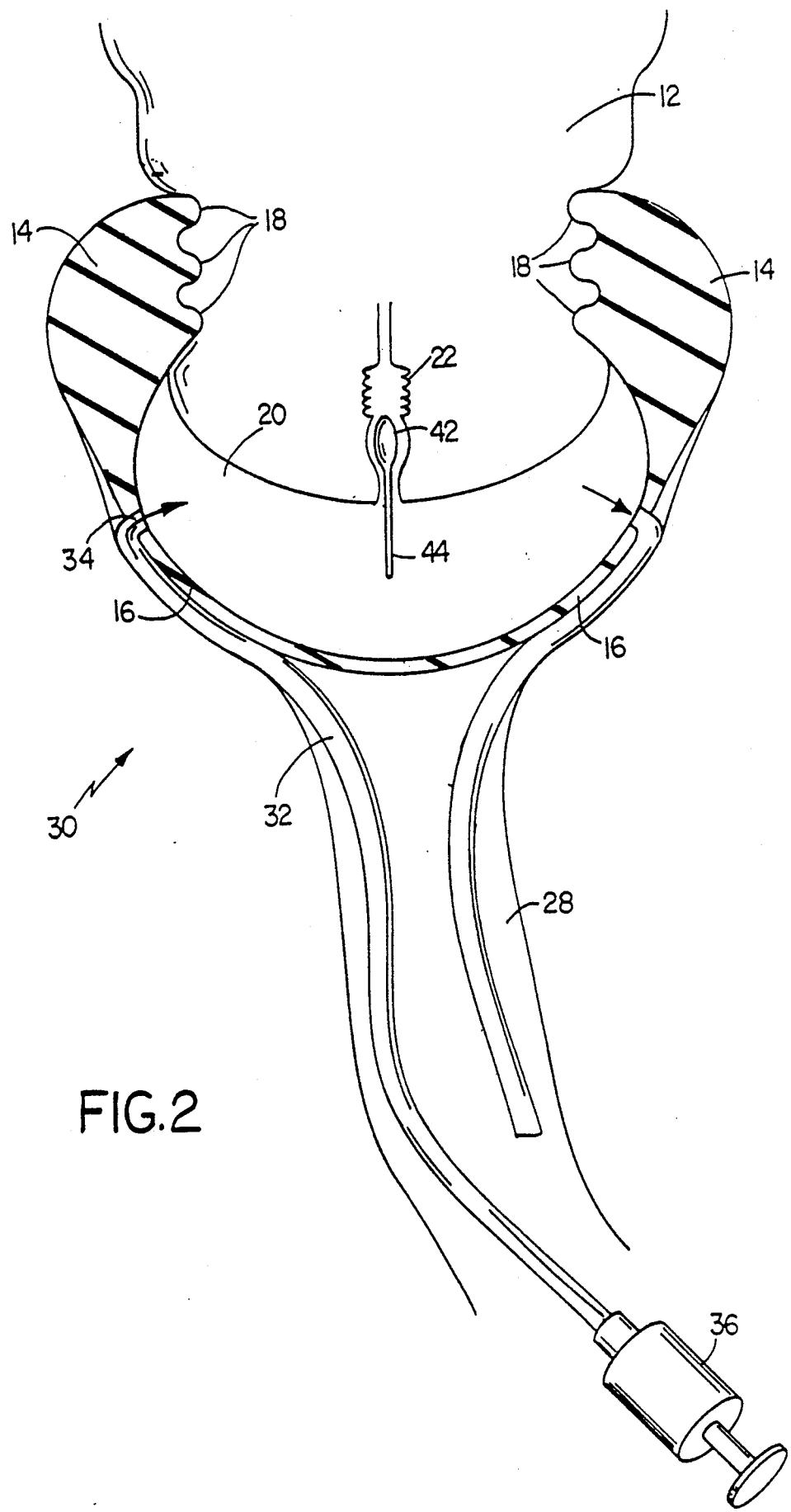
FIG. 2 is a cross-sectional view of a precursor contraceptive cervical cap fitted over a patient's cervix.

There is shown in FIG. 2 a precursor cap 30 secured to cervix 12 for use in preparing cap 10 (FIG. 1). Precursor cap 30 features an input tube 32 having two open ends and extending through vagina 28. One end of tube 32 is placed in an opening 34 in dome portion 16 that leads into gap 20. The other end of tube 32 is attached to a syringe 36 filled with liquid silicone polymer for filling gap 20.

The liquid silicone polymer in syringe 36 is injected into gap 20 through tube 32 until gap 20 is completely filled. During injection the cap is held in place with forceps sized to fit the cap. During the injection operation, excess polymer and air are vented through a vent tube 40 placed in an opening 38 leading into gap 20. Once in gap 20, the silicone polymer solidifies.

Marker 42 is a cotton tipped swab about 2 cm in length or similar device inserted in cervical canal 22 prior to placing cap 30 over cervix 12. Stick portion 44 typically protrudes approximately 5-10 mm from the opening of canal 22. As the silicone polymer solidifies in gap 20, stick portion 44 becomes embedded in the polymer. When cap 30 is removed from cervix 12, marker 42 (through stick portion 44) remains attached to cap 30, thus marking the location of the opening of canal 22.

Once cap 30 is removed from the body, tubes 32 and 40 are removed; openings 34 and 38 are sealed off by the solidified polymer. A passage approximately 2-10 mm in diameter is then drilled through the solid polymer and dome portion 16 at the point designated by marker 42 to form effluent canal 24 (FIG. 1); marker 42 thus permits effluent canal 24 to be aligned with cervical canal 22. Next, effluent tube 26 (FIG. 1) is attached to cap 30 e.g., by wedging one end between the solid polymer and the interior surface of dome portion 16 such that this end extends over the outer end of effluent canal 24. The finished cap (cap 10 in FIG. 1) is then reinserted over the patient's cervix.

Once cap 10 is in place, uterine and cervical discharges exit the body through effluent tube 26, but retrograde migration of sperm through tube 26 is prevented. Thus, cap 10 can remain in place for extended periods of time.

Figure 3:
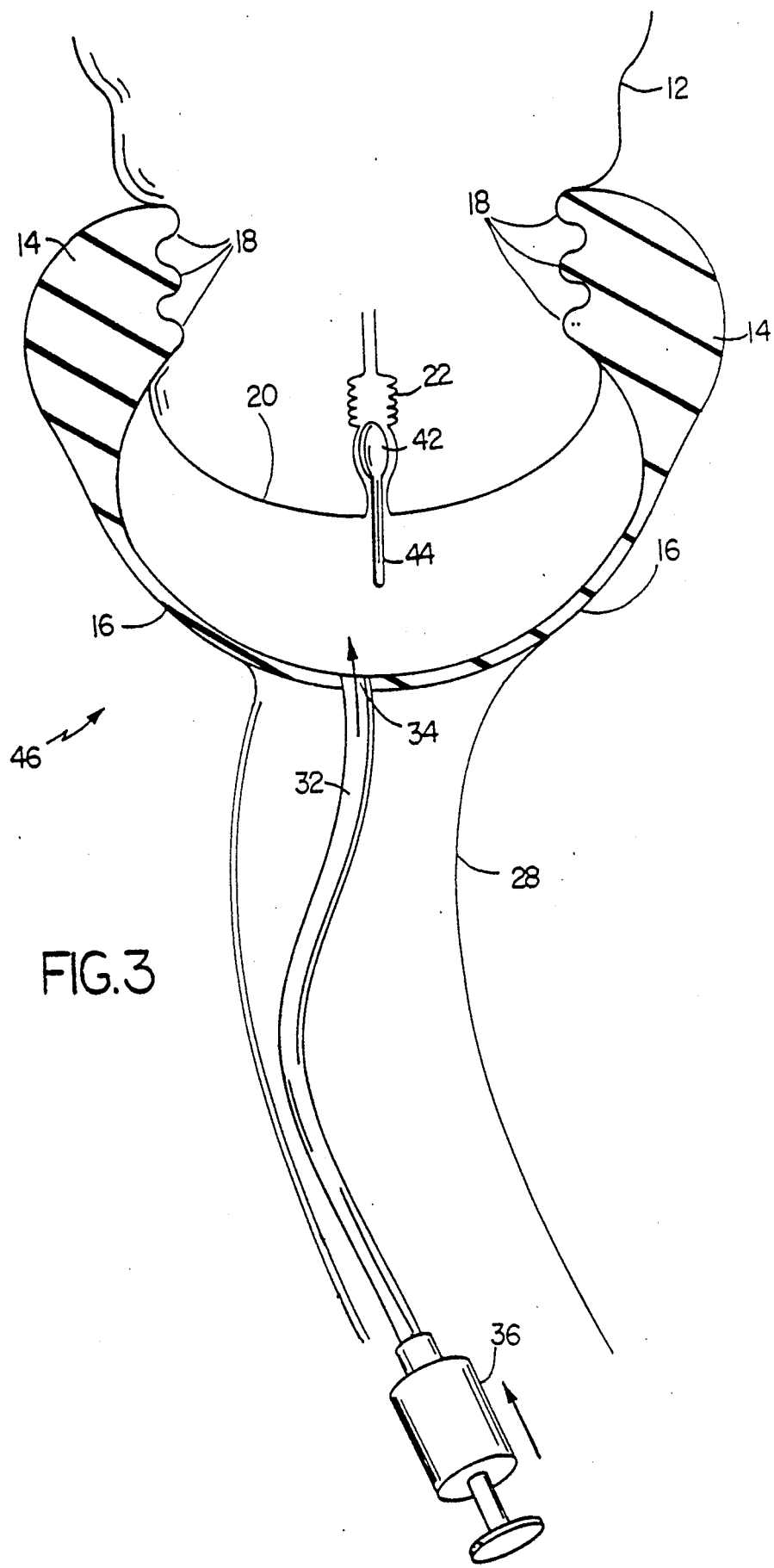
FIGS. 3 and 4 are cross-sectional views of a second precursor cap fitted over a patient's cervix, according to the process of the invention.

Referring to FIG. 3, there is shown a second precursor cap 46 for preparing the cervical cap 10 shown in FIG. 1. Precursor cap 46 is identical to precursor cap 30 shown in FIG. 2 except that it lacks vent tube 40.

Marker 42 is inserted in cervical canal 22 as described above prior to placing cap 46 over cervix 12. Next, cap 46 is gently placed loosely over cervix 12 so that space is left between the outer walls of cervix 12 and the rim portion 14 of the cap; thus, in contrast to the process described above for precursor cap 30, the cap is not sealed tightly around the cervix at this point. Syringe 34 is then filled with an amount of liquid silicone polymer in excess of that required to fill the gap (thus ensuring that a slight excess will spill out the perimeter of the cap through the space left between cervix 12 and the rim portion 14 of the cap) and the liquid polymer injected into gap 20 through tube 32 in the direction of the arrows until gap 20 is completely filled.

Figure 4:
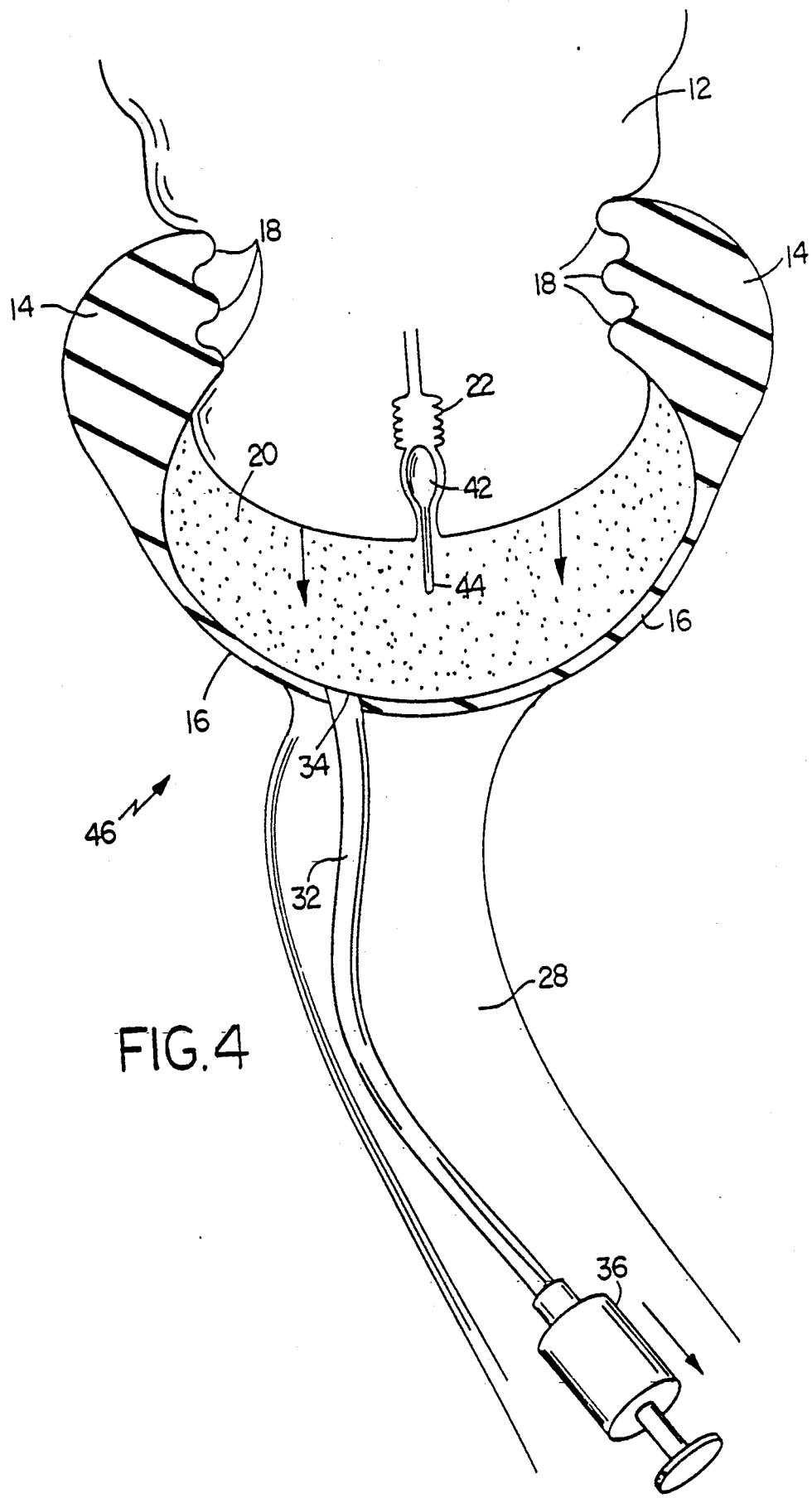

Referring to FIG. 4, once the gap has been completely filled, but before the liquid polymer has solidified, the cap is pushed firmly towards cervix 12 to form a tight seal. As soon as the seal is formed, the plunger of syringe 36 is retracted to withdraw an amount of liquid polymer approximately equal to the volume of the cervix (which has been determined for the individual patient prior to fitting the cap). The vacuum created by this action pulls cervix 12 (which has retreated due to pressure from the injection of the polymer) down out of the pelvis into the silicone polymer filling gap 20 and holds it there until the liquid polymer has solidified. This results in a deep impression of the complete cervix (rather than an impression of only the portions nearest cervical canal 22), and thus a better fitting, more stable cap. Once the polymer has solidified, the cap is removed and processed as described above to prepare the final cap.

Other embodiments are within the following claims.

For example, tube 26 can be infused with a spermicide (i.e. the spermicide is incorporated into the walls of tube 26). The spermicide then slowly diffuses through the walls of tube 26 over time to increase protection. The spermicide can also be incorporated directly into the biocompatible material from which it can diffuse over time through the walls and into the tube.

Instead of effluent tube 26, a conventional pressure-operated valve, e.g., a flap type membrane valve, can be used to effect discharge of menstrual fluid. Caps without ridged rim portions, e.g., commercially available Vimule, K-W, Dumas, and Prentif caps, can also be used.

After cap 30 (containing the gap-filling polymer and marker 42) is removed from the body, it can be used to form a mold by e.g., embedding in plaster to form a two-part mold that is a negative of the gap-filled cap. The mold is then filled with an appropriate elastomer, e.g., with polysiloxane, to prepare a cap made entirely from polysiloxane custom-fitted to patient's cervix in which the gap is already filled. The cap is then fitted to the patient's cervix, equipped with effluent tube 26 and inserted over the patient's cervix.

The effluent tube or pressure operated valve can also be eliminated to create a cap useful during the intemenstruum period.

Instead of forceps, the cap can be manipulated or held in place about the cervix by attaching a small suction cup (about 12 mm in diameter) to the dome portion of the cap. The suction cup is attached to a second syringe; withdrawing the plunger of the syringe creates a vacuum which acts upon the suction cup to hold the cap in place.

I claim:

1. A method of preparing a contraceptive cervical cap or a form therefor comprising the steps of providing a cervical cap comprising a rim portion for securing said cap to the cervix and a dome portion having input means for introducing a biocompatible material into said cap, said dome portion being spaced from the cervix when said cap is in place to form a gap between the interior surface of said dome portion and the cervix;

loosely placing said cap over the cervix while leaving an amount of space between said rim portion of said cap and the cervix through which excess biocompatible material can leave said cap;

filling said cap with said biocompatible material through said input means;

sealing the rim portion of the filled cap around the cervix; and withdrawing a predetermined amount of said biocompatible material through said input means to draw said cervix out into said biocompatible material.

2. The method of claim 1 wherein said rim portion comprises a plurality of ridges arranged along the interior surface of said rim portion to secure said cap to the cervix.

3. The method of claim 1 wherein said biocompatible elastomer comprises a silicone elastomer.

4. The method of claim 1 wherein said input means comprises a tube in communication with said dome portion of said cap and a syringe attached to said tube.

5. The method of claim 1 wherein said predetermined amount of biocompatible material withdrawn through said input means is about equal to the volume of the cervix.

6. The method of claim 1 further comprising the steps of inserting a marker into the cervical canal to mark the location of said canal prior to placing said cap over the cervix;

causing said marker to become embedded in said biocompatible material during introduction of said biocompatible material into said cap;

removing said cap from the cervix after withdrawing said predetermined amount of said biocompatible material; and creating an opening in said dome portion at the position of said marker, corresponding to the location of the cervical canal, to permit material to flow out of, but not into, the cervix and uterus through said cap.

* * * * *